US010517984B2

(12) United States Patent
DiLuccio et al.

(10) Patent No.: US 10,517,984 B2
(45) Date of Patent: Dec. 31, 2019

(54) ANTIMICROBIAL WOUND CLOSURE MATERIALS, INCLUDING ANTIMICROBIAL SUTURES, AND METHOD FOR CLOSING A WOUND USING THE SAME

(71) Applicant: CorMedix Inc., Bedminster, NJ (US)

(72) Inventors: Robert DiLuccio, Haymarket, VA (US); Z. Paul Lorenc, Bedminster, NJ (US); Randy Milby, Bedminster, NJ (US)

(73) Assignee: CorMedix Inc., Bedminster, NJ (US)

(*) Notice: Subject to any disclaimer, the term of this patent is extended or adjusted under 35 U.S.C. 154(b) by 0 days.

(21) Appl. No.: 15/240,447

(22) Filed: Aug. 18, 2016

(65) Prior Publication Data
US 2017/0049921 A1 Feb. 23, 2017

Related U.S. Application Data

(60) Provisional application No. 62/206,368, filed on Aug. 18, 2015, provisional application No. 62/292,597, filed on Feb. 8, 2016.

(51) Int. Cl.
| | | |
|---|---|---|
| *A61L 17/00* | (2006.01) | |
| *A61L 17/10* | (2006.01) | |
| *A61L 17/04* | (2006.01) | |
| *A61B 17/06* | (2006.01) | |
| *A61B 17/064* | (2006.01) | |

(52) U.S. Cl.
CPC .......... *A61L 17/005* (2013.01); *A61B 17/064* (2013.01); *A61B 17/06166* (2013.01); *A61L 17/04* (2013.01); *A61L 17/10* (2013.01); *A61B 2017/06176* (2013.01); *A61L 2300/404* (2013.01)

(58) Field of Classification Search
CPC .... A61K 31/54; A61K 2300/00; A61K 31/19; A61K 31/18; A61K 31/549; A61K 35/12; A61K 31/716; A61K 9/0051; A61K 9/0063; A61K 9/0092; A61K 9/06; A61L 2300/404; A61L 15/28; A61L 2300/204; A61L 15/46; A61L 2300/206; A61L 29/16; A61L 31/16; A61L 15/20; A61L 2300/64; A61L 15/18; A61L 2300/108; A61L 2430/06; A61L 27/3629; A61L 27/3654; A61L 27/3817; A61L 27/3852; A61L 15/325; A61L 15/42; A61L 15/425; A61L 15/44; A61L 2300/42; A61L 2300/45; A61L 2400/04; A61L 2430/02; A61L 26/0004; A61L 26/0033; A61L 26/0066; A61L 26/0085; A61L 27/14; A61L 27/24; A61L 27/54; A61L 27/56; A61L 29/14; A61L 31/04; A61L 31/146; A61M 27/00; A61M 37/00; A61M 39/0208; A61M 5/158; A61M 5/427; A61B 17/00491; A61B 17/3468; A61B 2017/00969
See application file for complete search history.

(56) References Cited

U.S. PATENT DOCUMENTS

| | | | |
|---|---|---|---|
| 861,231 A | 7/1907 | Clark | |
| 4,024,871 A | 5/1977 | Stephenson | |
| 5,997,568 A * | 12/1999 | Liu | A61L 17/12 525/408 |
| 6,878,757 B2 | 4/2005 | Roby | |
| 7,513,093 B2 | 4/2009 | Scalzo et al. | |
| 2003/0176848 A1 | 9/2003 | Gibson et al. | |
| 2007/0010856 A1 | 1/2007 | Cohen | |
| 2007/0098675 A1 | 5/2007 | Elisseeff et al. | |
| 2008/0177217 A1 | 7/2008 | Polaschegg | |
| 2010/0000196 A1 | 1/2010 | Indiano | |
| 2012/0041483 A1 * | 2/2012 | Indiano | A61B 17/06166 606/228 |
| 2012/0312860 A1 * | 12/2012 | Ming | A61B 17/00491 227/176.1 |
| 2013/0251774 A1 * | 9/2013 | Priewe | A61K 38/16 424/404 |

FOREIGN PATENT DOCUMENTS

| | | | | |
|---|---|---|---|---|
| DE | 102006001954 A1 * | 7/2007 | | A61L 15/44 |
| EP | 1897500 | 3/2008 | | |
| WO | WO 2005/115357 | 12/2005 | | |
| WO | WO 2011/053562 | 5/2011 | | |
| WO | WO 2013/049149 | 4/2013 | | |
| WO | WO 2013/128401 | 9/2013 | | |

OTHER PUBLICATIONS

Bryant et al., Manipulations in Hydrogel Chemistry Control Photoencapsulated Chondrocyte Behavior and Their Extracellular Matrix Production, Journal of Biomedical Materials Research, Nov. 6, 2003, pp. 1430-1436.
Chen et al., Research on the Interstitial Fluid Load Support Characteristics and Start-Up Friction Mechanisms of PVA-HA-Silk Composite Hydrogel, Journal of Bionic Engineering, 2014, vol. 11, pp. 378-388.
Curley et al., An Evaluation of the Thermal and Mechanical Properties of a Salt-Modified Polyvinyl Alcohol Hydrogel for a Knee Meniscus Application, Journal of the Mechanical Behavior of Biomedical Materials, 2014, vol. 40, pp. 13-22.
Gong et al., Double-Network Hydrogels with Extremely High Mechanical Strength, Advanced Materials, Jul. 17, 2003, vol. 15, No. 14, pp. 1155-1158.
Haque et al., Super Tough Double Network Hydrogels and Their Application as Biomaterials, Polymer, 2012, vol. 53, pp. 1805-1822.
Martens et al., Tailoring the Degradation of Hydrogels Formed from Multivinyl Poly(ethylene glycol) and Poly (vinyl alcohol) Macromers for Cartilage Tissue Engineering, Biomacromolecules, 2003, vol. 4, pp. 283-292.
Ng et al., A Novel Macroporous Polyvinyl Alcohol Scaffold Promotes Chondrocyte Migration and Interface Formation in an In Vitro Cartilage Defect Model, Tissue Engineering, 2012, vol. 18, Nos. 11 and 12, pp. 1273-1281.
Shi et al., Effect of Irradiation Dose on Mechanical and biotribological Properties of PVA/PVP Hydrogels as Articular Cartilage, Tribology International, 2014, vol. 78, pp. 60-67.

(Continued)

*Primary Examiner* — Audrea B Coniglio
(74) *Attorney, Agent, or Firm* — Pandiscio & Pandiscio

(57) ABSTRACT

An antimicrobial suture comprising a filament and taurolidine.

31 Claims, 11 Drawing Sheets

(56) References Cited

OTHER PUBLICATIONS

Sridhar et al., Development of a Cellularly Degradable PEG Hydrogel to Promote Articular cartilage Extracellular Matrix Deposition, Advanced Healthcare Materials, 2015, vol. 4, pp. 702-713.

Tan et al., Injectable in situ Forming Biodegradable Chitosan-Hyaluronic Acid based Hydrogeis for Cartilage Tissue Engineering, Biomaterials, 2009, vol. 30, pp. 2499-2506.

Block, R.J., Proteins of the Nervous System: Considered in the Light of the Prevailing Hypotheses on Protein Structure, Yale Journal of Biology and Medicine, May 1937, vol. 9, No. 5, pp. 445-503.

Ford, H.R. et al., Intraoperative Handling and Wound Healing: Controlled Clinical Trial Comparing Coated VICRYL Plus Antibacterial Suture (Coated Polyglactin 910 Suture with Triclosan) with Coated VICRYL Suture (Coated Polyglactin 910 Suture), Surgical infections, 2005, vol. 6, No. 3, pp. 313-321.

Hvass, A. et al., Determination of Protamine Peptides in insulin Drug Products Using Reversed Phase High Performance Liquid Chromatography, Journal of Pharmaceutical and Biomedical Analysis, 2005, vol. 37, No. 3, pp. 551-557.

Mori, Y. et al., Preparation and Characterization of Low-Molecular-Weight Heparin/Protamine Nanoparticles (LMW-H/P NPs) as FGF-2 Carrier, International Journal of Nanomedicine, 2010, vol. 5, pp. 147-155.

Polymedix Press Release, New Grant Supports Development of Antimicrobial Sutures to Combat Infection, Jun. 11, 2010.

Storch, M.L. et al., Experimental Efficacy Study of Coated VICRYL Plus Antibacterial Suture in Guinea Pigs Challenged with *Staphylococcus aureus*, Surgical Infections, 2004, vol. 5, No. 3, pp. 281-288.

\* cited by examiner

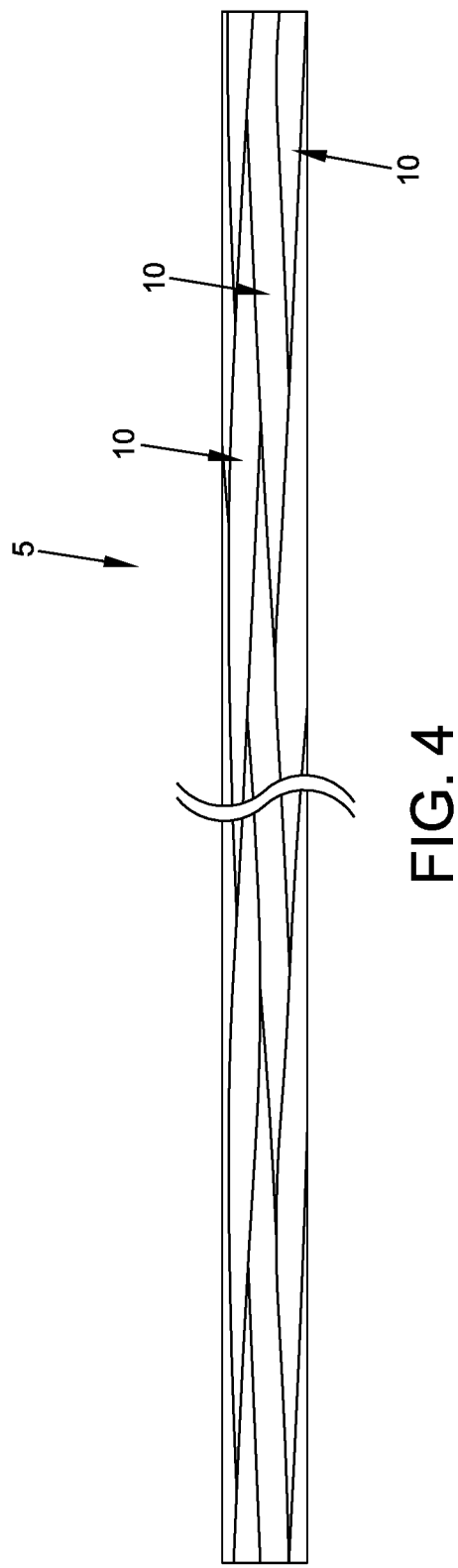
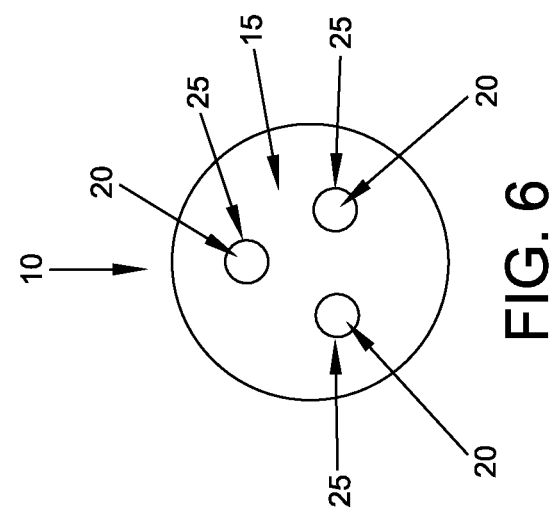
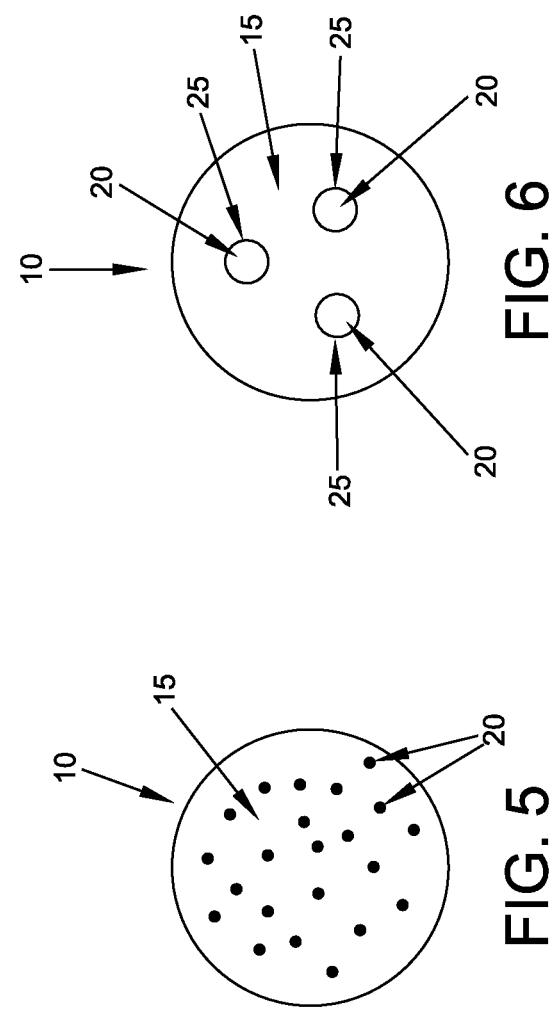

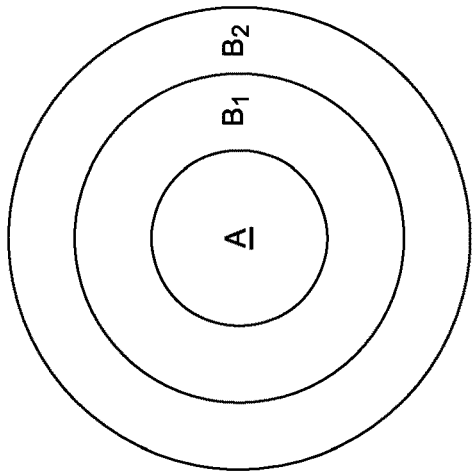

FIG. 11

Embodiment 1: A= Taurolidine, B= No Taurolidine
Embodiment 2: B= Taurolidine, A= No Taurolidine

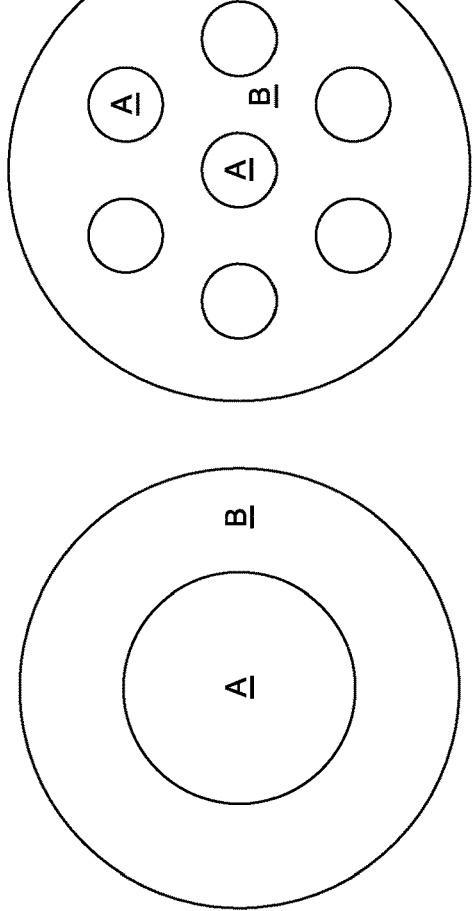

FIG. 12

Embodiment 1: A= Taurolidine, B= No Taurolidine
Embodiment 2: B= Taurolidine, A= No Taurolidine

FIG. 13

Embodiment 1: A=Taurolidine, B1=no Taurolidine, B2=no Taurolidine
Embodiment 2: A=Taurolidine, B1= Taurolidine, B2=no Taurolidine
Embodiment 3: A=Taurolidine, B1= Taurolidine, B2= Taurolidine
Embodiment 4: A=No Taurolidine, B1= Taurolidine, B2=no Taurolidine
Embodiment 5: A=No Taurolidine, B1= no Taurolidine, B2= Taurolidine
Embodiment 6: A=No Taurolidine, B1= Taurolidine, B2= Taurolidine

| Fiber | PA01 | SA BAA 44 | S. epi 35984 |
|---|---|---|---|
| 2% taurolidine in poly ε-caprolactone | 2 | 2 | 0 |
| 6% taurolidine in poly ε-caprolactone | 2 | 3 | 4 |
| 10% taurolidine in poly ε-caprolactone | 2 | 4.75 | 9.25 |
| CONTROL (0% drug in ρ-dioxanone) | 0 | 0 | 0 |
| 2% taurolidine in ρ-dioxanone | 1.2 | 1.2 | 3.25 |
| 6% taurolidine in ρ-dioxanone | 5.5 | 7.75 | 8.75 |
| 10% taurolidine in ρ-dioxanone | 7.25 | 10.125 | 10.25 |

FIG. 14

C= ε-caproiactone fibers
D= p-dioxanone fibers

| Raw Material | Composition (Weight Percent) | | | | | | | |
| --- | --- | --- | --- | --- | --- | --- | --- | --- |
| | 1 | 2 | 3 | 4 | 5 | 6 | 7 | 8 |
| Taurolidine | 100% | 2% | 6% | 10% | | 2% | 6% | 10% |
| Glycomaxx GC 7525 | | 98% | 94% | 90% | | | | |
| Glycomaxx GL 910 | | | | | 100% | 98% | 94% | 90% |

FIG. 20

ANTIMICROBIAL WOUND CLOSURE MATERIALS, INCLUDING ANTIMICROBIAL SUTURES, AND METHOD FOR CLOSING A WOUND USING THE SAME

REFERENCE TO PENDING PRIOR PATENT APPLICATIONS

This patent application:

(i) claims benefit of prior U.S. Provisional Patent Application Ser. No. 62/206,368, filed Aug. 18, 2015 by CorMedix Inc. and Robert DiLuccio et al. for ANTIMICROBIAL WOUND CLOSURE MATERIALS, INCLUDING ANTIMICROBIAL SUTURES; and (ii) claims benefit of prior U.S. Provisional Patent Application Ser. No. 62/292,597, filed Feb. 8, 2016 by CorMedix Inc. and Robert DiLuccio et al. for ANTIMICROBIAL WOUND CLOSURE MATERIALS, INCLUDING ANTIMICROBIAL SUTURES.

The two (2) above-identified patent applications are hereby incorporated herein by reference.

FIELD OF THE INVENTION

This invention relates to sutures, staples and the like used in medical applications, and more particularly to sutures, staples and the like having antimicrobial properties.

BACKGROUND OF THE INVENTION

Sutures are commonly used for closing wounds and/or surgical site incisions, or to repair tissue that has torn. When using a suture, it is important to avoid infection. Although surgeries and wound closings are often performed under sterile conditions, surgical site infections (SSIs) are the third most commonly acquired hospital infection, and may be associated with severe morbidity and mortality. Since more than sixty percent (60%) of SSIs occur in the area of the incision, the use of sutures having antimicrobial properties has the potential to be useful in combating such infections and, ultimately, improving patient outcomes by reducing the amount and severity of these SSI-type infections.

Sutures having antimicrobial properties currently exist. At the present time, the industry leader in the antimicrobial suture market is Ethicon, a Johnson & Johnson company. Johnson & Johnson's Ethicon antibacterial sutures rely primarily on a Triclosan-type antimicrobial agent.

Triclosan is a chlorinated phenolic biocide antiseptic that, according to Johnson & Johnson, has a different mode of action than traditional antibiotics. It is a "phenol" with multi-targeted biocidal mechanisms that are believed to have non-specific effects that act on cell membrane activities to kill undesired microbes. It is also believed that Triclosan blocks the active site of the Enoyl-acyl carrier protein reductase (ENR) that is an essential enzyme in fatty acid synthesis, used in building cellular components and in cell reproduction.

Ethicon's Triclosan-coated sutures appear to be able to perform their antimicrobial function in a manner similar to counterparts that do not contain Triclosan. To date, published data exists to suggest that Triclosan inhibits bacteria colonization of a suture. See, Ford H R, Jones P, Reblock K, Simpkins D L, "Intra-operative Handling and Wound Healing Characteristics of Coated Polyglatin 910 Antibacterial Suture and Coated Polyglactin 910 Suture". Surg. Infec. 2005; 6; 313-21.

Additionally, an in vivo study of Ethicon's Triclosan-coated sutures (i.e., Ethicon's VICRYL Plus™ antibacterial sutures) showed that they have an inhibitory or bactericidal activity against *Staphylococcus aureus*, Methicillin-Resistant *S. Aureus* (MRSA), *S. Epidermidis* (Biofilm-Positive) and *E. coli*. See, Storch M L, Rothenberger S J, Jacinto G, "Experimental Efficacy Study of Coated VICRYL+Antibacterial Suture in Guinea Pigs Challenged with *Staphylococcus Aureus*". Surg. Infect. J. 2004; 5; 2A1-288.

Additional information about Ethicon's Triclosan-coated sutures can be found on Ethicon's web site at http://www-.plussutures.com. Additional discussions of Ethicon's antimicrobial sutures can be found in Stephenson, U.S. Pat. No. 4,024,871 (24 May 1997) and Scalzo et al., U.S. Pat. No. 7,513,093 (7 Apr. 2009). In particular, the reader's attention is directed to the prior art discussions in each of these Ethicon patents, as a wide variety of various antimicrobial agents and methods for incorporating antimicrobial agents into sutures are discussed therein.

The Tyco Healthcare Group of Covidien plc has also been active in the antimicrobial suture field. An example of a Tyco antimicrobial suture is discussed in Robey, U.S. Pat. No. 6,878,757 (12 Apr. 2005), which discloses an antimicrobial suture coating that contains a fatty acid ester salt mixed with a bioabsorbable co-polymer.

Another Tyco antimicrobial suture patent application is Cohen, U.S. Patent Application Publication No. US2007/0010856 A1, published 11 Jan. 2007. Cohen's antimicrobial suture includes a plurality of filaments with interstitial spaces defined by the plurality of filaments, and an antimicrobial solution disposed within the interstitial spaces. An antimicrobial coating is placed on at least a portion of the plurality of filaments. The preferred antimicrobial agent used in Cohen is an antiseptic, film-forming polymer, and a salt of a fatty acid ester. Examples of the same are given in paragraph [0014] of the aforementioned published Cohen patent application.

Additionally, Polymedix, Inc. has developed an antimicrobial suture. The Polymedix suture employs PolyCide® polymers that are described as "novel defensin-mimetic compounds" which are synthetic mimetics of the host offense proteins that (according to Polymedix) are one of the oldest and most effective antimicrobial defense systems found in humans and virtually all living creatures. These PolyCides® are alleged to have a mechanism of action that directly disrupts the bacterial cell membranes and makes the development of bacterial resistance unlikely to occur. More information about these antimicrobial sutures can be found at www.polymedix.com. See also the Polymedix press release dated 11 Jun. 2010 "New Grant Supports Development of Antimicrobial Sutures to Combat Infection" (http://www.newswise.com/articles).

Silver is another compound having well known antimicrobial properties, and silver has been used to provide particular articles with antimicrobial properties. One early example of silver being used in a ligature is shown in Clark, U.S. Pat. No. 861,231 (23 Jul. 1907). Clark created a surgical ligature that was soaked in an antiseptic salt that preferably comprised an iodide of silver as the salt.

Another example of the use of silver to create an antimicrobial product is shown in Indiano, U.S. Patent Application Publication No. 2010/0000196, published 7 Jan. 2010. In Indiano, a textile product (non-suture related) incorporates silver to render the product antimicrobial.

Although the above-referenced products presumably perform their intended function, room for improvement exists. In particular, there is a need for a novel antimicrobial suture that is both capable of having significant antimicrobial properties and that can be produced at a reasonable cost, to provide a cost-effective deterrent to infections.

SUMMARY OF THE INVENTION

In accordance with the present invention, a novel suture having antimicrobial properties is provided. The antimicrobial properties of the suture are provided by incorporating taurolidine in the suture.

The novel suture may comprise one or more filaments and taurolidine carried by the one or more filaments.

The one or more filaments may be in the form of a monofilament structure or a multifilament structure. Where the one or more filaments are in a multifilament structure, the one or more filaments may be joined together (e.g., by welding them together after extrusion or by braiding them together), or the one or more filaments may be co-extruded as a composite structure.

The taurolidine may be carried by the one or more filaments by substantially evenly dispersing the taurolidine within the matrix of a filament, or by positioning the taurolidine within one or more regions of the matrix of the filament (e.g., by co-extruding a matrix containing the taurolidine with the base matrix of the filament), or by positioning the taurolidine on the surface of the filament (e.g., by coating or co-extruding) or, in the case of a multifilament suture, by positioning the taurolidine within the interstitial spaces of the suture (i.e., in the interstitial spaces between the filaments comprising the multifilament suture) or, where a filament is absorbent, by introducing a taurolidine solution into the filament, etc.

(As used herein, the terms "matrix" and "matrix material" are intended to mean a polymer or other material which may be extruded through a die or otherwise processed so as to form a filament.)

The sutures of the present invention may be absorbable or non-absorbable, and may come in a range of different sizes.

Absorbable Sutures.

Absorbable suture materials which may be used to form the novel suture of the present invention include, for example, catgut (collagen sutures derived from sheep intestinal submucosa), reconstituted collagen, polyglycolide (PGA), poly(glycolide-lactide) random copolymer (Vicryl®), poly-p-dioxanone (PDS®, PDSII®), poly(glycolide-trimethylene carbonate block copolymer (Maxon®), poly(glycolide-e-caprolactone)(Monocryl®), and glycolide-dioxanone-trimethylene carbonate triblock copolymer (Biosyn®).

Non-Absorbable Sutures.

Non-absorbable suture materials which may be used to form the novel suture of the present invention include filaments comprising natural fibers (e.g., silk, cotton and linen) and filaments comprising synthetic fibers (e.g., polyethylene, polypropylene, polyamide, polyester, poly(tetrafluroethylene)(Gore-Tex®), and stainless steel).

Suture Size.

The novel suture of the present invention may be provided in a range of different sizes. More particularly, two standards are commonly used to describe the size of suture materials: United States Pharmacopoeia (USP) and European Pharmacopoeia (EP).

The USP standard is the most commonly used. In the USP standard, the size is represented by one or more Arabic numerals: size 0 has a diameter of 0.4 mm (for collagen suture); sizes larger than 0.4 mm (for collagen suture) have an ascending Arabic numeral, e.g., size 1 has a diameter of 0.5 mm (for collagen), size 2 has a diameter of 0.6 mm (for collagen), etc.; and sizes smaller than 0.4 mm (for collagen suture) have an ascending Arabic numeral followed by "–0" (or "/0"), e.g., size 2-0 has a diameter of 0.35 mm (for collagen), size 3-0 has a diameter of 0.3 mm (for collagen), etc.

Because a range of diameters is permitted for each USP suture size, the tensile strength of sutures having the same USP size, but formed out of different materials, may be different from each other. By way of example but not limitation, two polypropylene sutures of the same USP size from two different manufacturers may have different tensile strengths because of a possible difference in suture cross-sectional area due to slightly different diameters. Furthermore, a polypropylene suture produced by a first manufacturer and having a smaller diameter may have a higher tensile breaking strength than another polypropylene suture produced by a second manufacturer and having a larger diameter. Additionally, for example, sutures made of certain materials can have their physical properties altered by either annealing or orientation.

Where an active ingredient is to be incorporated into a suture, it is generally best to optimize the loading of the active ingredient in the suture by either placing the active ingredient within the matrix of a filament of the suture (e.g., by dispersing the active ingredient within the matrix of the suture or by co-extruding a matrix containing the active ingredient with the base matrix of the filament), or on the surface of a filament of the suture (e.g., as a coating), or in a sheath co-extruded with a filament of the suture (e.g., by co-extruding a matrix containing the active ingredient with the base matrix of the filament) or, in the case of a multifilament suture, within the interstitial spaces of the suture (i.e., in the interstitial spaces between the filaments comprising the multifilament suture) or, where the filament of the suture is absorbent, by introducing a taurolidine solution into the filament, etc. In this way, the physical properties of the suture can be maintained.

Accordingly, with the present invention, taurolidine is incorporated within the matrix of a filament of the suture (e.g., by dispersing the taurolidine within the matrix of the suture or by co-extruding a matrix containing the taurolidine with the base matrix of the filament), or disposed on the surface of a filament of the suture (e.g., as a coating), or in a sheath co-extruded with a filament of the suture (e.g., by co-extruding a matrix containing the taurolidine with the base matrix of the filament), or in the case of a multifilament suture, within the interstitial spaces of the suture (i.e., the interstitial spaces between the filaments comprising the multifilament suture) or, where the filament of the suture is absorbent, by introducing a taurolidine solution into the filament, etc.

In accordance with another aspect of the present invention, a method is also provided for manufacturing a suture having antimicrobial properties. The antimicrobial properties are provided by incorporating taurolidine in the suture. In accordance with the present invention, the method for manufacturing a suture having antimicrobial properties comprises mixing the taurolidine in the matrix of a filament of the suture, or co-extruding the taurolidine in one or more areas within a filament of the suture (e.g., by co-extruding a matrix containing the taurolidine with the base matrix of the filament), or coating the taurolidine on the surface of a filament of the suture, or co-extruding the taurolidine as a sheath over a filament of the suture (e.g., by co-extruding a matrix containing the taurolidine with the base matrix of the filament) or, in the case of a multifilament suture, by positioning the taurolidine within the interstitial spaces of the suture (i.e., in the interstitial spaces between the filaments comprising the multifilament suture) or, where the filament is absorbent, by introducing a taurolidine solution into the filament, etc.

It should be appreciated that where the taurolidine is to be added to the suture through a co-extrusion process, it is often desirable to provide (i) a matrix comprising the taurolidine (i.e., a "taurolidine-containing matrix"), and (ii) the base matrix of the filament, and then to co-extrude the "taurolidine-containing matrix" with the base matrix of the filament, whereby to form an antimicrobial filament for the antimicrobial suture.

In one preferred form of the invention, the matrix material incorporating the taurolidine is the same as the matrix material comprising the remainder of the filament. This helps to avoid the creation of "phase changes" at the interface of the taurolidine-containing matrix and the matrix material of the remainder of the filament.

However, it should also be appreciated that, if desired, the matrix material incorporating the taurolidine may be different than the matrix material of the remainder of the filament.

And it should be appreciated that where a filament comprises a porous structure (e.g., as may be the case with certain natural fibers), the filament may be exposed to a solution containing taurolidine so that the taurolidine enters into the porous structure of the filament. The resulting suture may be packaged "wet" (i.e., dampened or immersed in a solution containing taurolidine) or it may be packaged "dry" (i.e., having been desiccated so as to remove the liquid, leaving only the taurolidine within the porous structure of the filament).

The novel suture of the present invention is configured to have good "suture" properties, including sufficient tensile strength to avoid breakage and sufficient bendability and malleability to be able to act like highly-bendable thread, while still possessing the antimicrobial activities provided by the taurolidine.

And the novel suture of the present invention is configured so that the weight percent of taurolidine in the suture is at least about 1%, and preferably higher, so as to provide significant antimicrobial properties while allowing the sutures to retain their desired physical properties.

Additionally, novel staples incorporating taurolidine are also provided in accordance with the present invention.

In one preferred form of the invention, there is provided an antimicrobial suture comprising at least one filament and taurolidine carried by the at least one filament.

In one preferred form of the invention, the at least one filament comprises a single filament.

In one preferred form of the invention, the least one filament comprises a plurality of filaments.

In one preferred form of the invention, the plurality of filaments adhere to one another so as to constitute a singular structure.

In one preferred form of the invention, the plurality of filaments are co-extruded so as to form a composite structure.

In one preferred form of the invention, the plurality of filaments are braided together so as to constitute a singular structure.

In one preferred form of the invention, the at least one filament is resorbable.

In one preferred form of the invention, the at least one filament is non-resorbable.

In one preferred form of the invention, the at least one filament comprises a polymer.

In one preferred form of the invention, the at least one filament comprises a homopolymer.

In one preferred form of the invention, the at least one filament comprises a copolymer.

In one preferred form of the invention, the at least one filament comprises a material selected from the group consisting of polyglycolide (PGA), poly(glycolide-lactide) random copolymer (Vicryl®), poly-p-dioxanone (PDS®, PDSII®), poly(glycolide-trimethylene carbonate block copolymer (Maxon®), poly(glycolide-e-caprolactone) (Monocryl®), glycolide-dioxanone-trimethylene carbonate triblock copolymer (Biosyn®), polyethylene, polypropylene, poly(tetrafluroethylene)(Gore-Tex®), stainless steel, polyesters, polyester-ethers, polyester-carbonates, polyamides, polyolephins, fluoropolymers, catgut, collagen, reconstituted collagen, cotton, linen and silk.

In one preferred form of the invention, the at least one filament comprises a matrix of material.

In one preferred form of the invention, the taurolidine is disposed within the matrix of material.

In one preferred form of the invention, the taurolidine is substantially evenly dispersed within the matrix of material.

In one preferred form of the invention, the taurolidine is restricted to one or more regions of the matrix of material.

In one preferred form of the invention, the at least one filament is extruded, and the taurolidine is co-extruded with the at least one filament.

In one preferred form of the invention, the taurolidine is disposed as a coating on the at least one filament.

In one preferred form of the invention, the coating is co-extruded with the at least one filament.

In one preferred form of the invention, the antimicrobial suture further comprises an overcoating disposed on top of the coating of taurolidine.

In one preferred form of the invention, the antimicrobial suture comprises multiple filaments, and the taurolidine is positioned in the interstitial spaces between the filaments.

In one preferred form of the invention, the antimicrobial suture comprises at least one filament which is absorbent, and a taurolidine solution is introduced into the at least one filament.

In one preferred form of the invention, the proportion of taurolidine in the antimicrobial suture constitutes greater than about 1% by weight.

In one preferred form of the invention, the proportion of taurolidine in the antimicrobial suture constitutes greater than about 2% by weight.

In one preferred form of the invention, the proportion of taurolidine in the antimicrobial suture constitutes greater than about 6% by weight.

In one preferred form of the invention, the proportion of taurolidine in the antimicrobial suture constitutes greater than about 10% by weight.

In one preferred form of the invention, the antimicrobial suture further comprises barbs.

In another preferred form of the invention, there is provided a method for treating a wound, the method comprising:

providing an antimicrobial suture comprising at least one filament and taurolidine carried by the at least one filament; and treating the wound with the antimicrobial suture.

In another preferred form of the invention, there is provided an antimicrobial surgical staple comprising:

a surgical staple; and taurolidine carried by the surgical staple.

In another preferred form of the invention, there is provided a method for treating a wound, the method comprising:

providing an antimicrobial surgical staple, the antimicrobial surgical staple comprising a surgical staple and taurolidine carried by the surgical staple; and treating the wound with the antimicrobial surgical staple.

BRIEF DESCRIPTION OF DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 4 is a schematic view of a novel antimicrobial suture formed in accordance with the present invention;

FIG. 5 is a schematic view of a novel filament formed in accordance with the present invention;

FIG. 6 is a schematic view of another novel filament formed in accordance with the present invention;

FIG. 11 is a schematic view showing two possible configurations for the present invention;

FIG. 12 is a schematic view showing two other possible configurations for the present invention;

FIG. 13 is a schematic view showing six other possible configurations for the present invention;

FIG. 14 is a table summarizing Zone of Inhibition studies for filaments carrying various levels of taurolidine when exposed to some exemplary microorganisms;

FIG. 20 is a table showing other examples of sutures formed in accordance with the present invention.

DETAILED DESCRIPTION OF THE PREFERRED EMBODIMENTS

Figure 1:
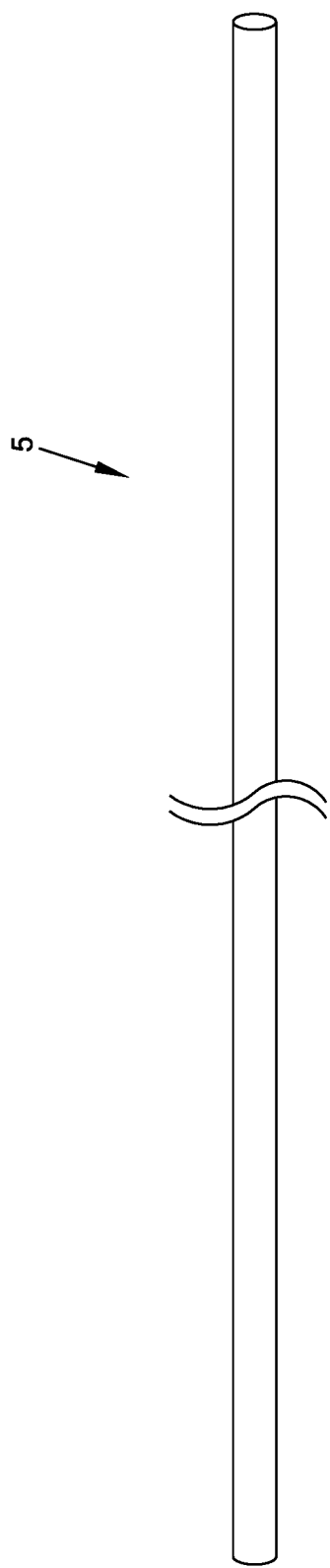
FIG. 1 is a schematic view of a novel antimicrobial suture formed in accordance with the present invention.

As noted above, prior art antimicrobial sutures are known in the art. It is beneficial to incorporate antimicrobial properties into sutures to combat the growth of microbes and germs, and to combat the creation and spread of infections by these microbes and germs. Such infections are complicating and deleterious events that often accompany wounds or surgical sites. By killing microbes and/or retarding the growth of microbes, one reduces the chance and/or severity of infection, thus helping to speed the healing process and increasing the success rates of procedures. Sutures are commonly used to close a wound or surgical site. Therefore, providing antimicrobial properties to sutures offers the opportunity to reduce infections associated with wounds or surgical sites.

In accordance with the present invention, taurolidine is incorporated in a suture so as to provide antimicrobial properties to the suture.

Taurolidine (bis(1,1-dioxoperhydro-1,2,4-thiadiazinyl-4)-methane) has antimicrobial and antilipopolysaccharide properties. It is derived from the amino acid taurine. The immunomodulatory action of taurolidine is reported to be mediated by priming and activation of macrophages and polymorphonuclear leukocytes.

Taurolidine has been used to treat patients with peritonitis and as an antiendoxic agent in patients with systemic inflammatory response syndrome. Taurolidine is a life-saving antimicrobial for severe abdominal sepsis and peritonitis. Taurolidine is active against a wide range of microorganisms that include gram positive bacteria, gram negative bacteria, fungi, mycobacteria and also bacteria that are resistant to various antibiotics such as MRSA, VISA, VRSA, ORSA, VRE, etc. Additionally, taurolidine demonstrates some anti-tumor properties, with positive results seen in early-stage clinical investigations using the drug to treat gastrointestinal malignancies and tumors of the central nervous system.

Taurolidine is also used as the active ingredient of antimicrobial catheter lock solutions for the prevention and treatment of catheter-related blood stream infections (CRBSIs) and is suitable for use in all catheter-based vascular access devices.

Bacterial resistance against taurolidine has not been observed in various studies to date.

Taurolidine acts by a non-selective chemical reaction. In aqueous solution, the parent molecule taurolidine forms equilibrium with taurultam and N-hydroxymethyl taurultam, with taurinamide being a downstream derivative.

The active agents of taurolidine are N-methylol derivatives of taurultam and taurinamide, which react with the bacterial cell wall, cell membrane, and proteins as well as with the primary amino groups of endo- and exotoxins. Microbes are killed and the resulting toxins are inactivated; the destruction time in vitro is 30 minutes.

Pro-inflammatory cytokines and enhanced TNF-α levels are reduced when taurolidine is used as catheter lock solution.

Taurolidine decreases the adherence of bacteria and fungi to host cells by destroying the fimbriae and flagella and thus prevents the formation of biofilms.

A dose of 5 g of taurolidine over 2 hours, every 4 hours, for at least 48 hours, was given intravenously for the treatment of various sepsis condition and beneficial results were observed.

The present invention comprises the provision and use of a novel antimicrobial suture wherein the novel antimicrobial suture may comprise one or more filaments and taurolidine carried by the one or more filaments.

The one or more filaments may be in the form of a monofilament structure or a multifilament structure. Where the one or more filaments are in a multifilament structure, the one or more filaments may be joined together (e.g., by welding them together after extrusion or by braiding them together), or the one or more filaments may be co-extruded as a composite structure.

The taurolidine may be carried by the one or more filaments by substantially evenly dispersing the taurolidine within the matrix of a filament, or by positioning the taurolidine within one or more regions of the matrix of the filament (such as by co-extruding a matrix containing the taurolidine with the base matrix of the filament), or by positioning the taurolidine on the surface of the filament (e.g., by coating or co-extruding) or, in the case of a multifilament suture, by positioning the taurolidine within the interstitial spaces of the suture (i.e., the interstitial spaces between the filaments comprising the multifilament suture) or, where a filament is absorbent, by introducing a taurolidine solution into the filament.

In one preferred form of the invention, and looking now at FIG. 1, there is provided an antimicrobial suture 5 comprising at least one filament and taurolidine carried by the at least one filament.

Figure 2:
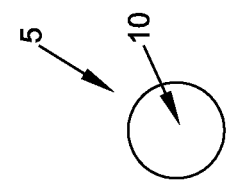
FIG. 2 is a schematic view of a novel antimicrobial suture formed in accordance with the present invention.

In one preferred form of the invention, and looking now at FIG. 2, the antimicrobial suture comprises a single filament 10 (and taurolidine carried by the single filament 10).

Figure 3:
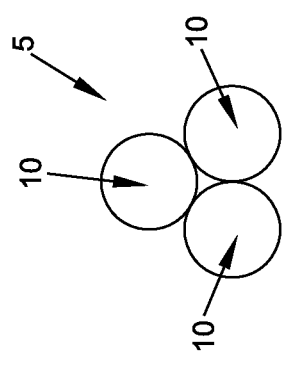
FIG. 3 is a schematic view of a novel antimicrobial suture formed in accordance with the present invention.

In another preferred form of the invention, and looking now at FIG. 3, the antimicrobial suture comprises a plurality of filaments 10 (and taurolidine carried by one or more of the plurality of filaments 10).

In one preferred form of the invention, the plurality of filaments 10 adhere to one another so as to constitute a singular structure.

In one preferred form of the invention, the plurality of filaments are co-extruded so as to form a composite structure.

In one preferred form of the invention, and looking now at FIG. 4, the plurality of filaments 10 are braided together so as to constitute a singular structure.

In one preferred form of the invention, the at least one filament is resorbable.

In one preferred form of the invention, the at least one filament is non-resorbable.

In one preferred form of the invention, the at least one filament comprises a polymer.

In one preferred form of the invention, the at least one filament comprises a homopolymer.

In one preferred form of the invention, the at least one filament comprises a copolymer.

In one preferred form of the invention, the at least one filament comprises a material selected from the group consisting of polyglycolide (PGA), poly(glycolide-lactide) random copolymer (Vicryl®), poly-p-dioxanone (PDS®, PDSII®), poly(glycolide-trimethylene carbonate block copolymer (Maxon®), poly(glycolide-e-caprolactone) (Monocryl®), glycolide-dioxanone-trimethylene carbonate triblock copolymer (Biosyn®), polyethylene, polypropylene, poly(tetrafluroethylene)(Gore-Tex®), stainless steel, polyesters, polyester-ethers, polyester-carbonates, polyamides, polyolephins, fluoropolymers, catgut, collagen, reconstituted collagen, cotton, linen and silk.

In one preferred form of the invention, and looking now at FIG. 5, the at least one filament 10 comprises a matrix 15 of material, and the taurolidine 20 is substantially evenly dispersed within the matrix of material.

In one preferred form of the invention, and looking now at FIG. 6, the taurolidine 20 is restricted to one or more regions 25 of the matrix 15 of material.

In one preferred form of the invention, the at least one filament is extruded, and the taurolidine is co-extruded with the at least one filament.

In one preferred form of the invention, the taurolidine is co-extruded with the at least one filament, wherein the taurolidine is contained within a matrix which comprises matrix material plus taurolidine, and wherein the taurolidine-incorporating matrix material is the same matrix material as the remainder of the filament.

In one preferred form of the invention, the taurolidine is co-extruded with the at least one filament, wherein the taurolidine is contained within a matrix which comprises matrix material plus taurolidine, and wherein the taurolidine-incorporating matrix material is a different matrix material than the remainder of the filament.

Figure 7:
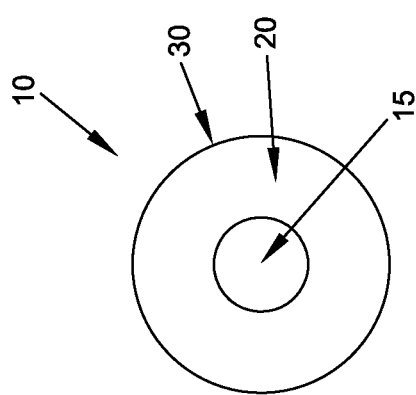
FIG. 7 is a schematic view of another novel filament formed in accordance with the present invention.

In one preferred form of the invention, and looking now at FIG. 7, the taurolidine 20 is disposed as a coating 30 on the at least one filament.

In one preferred form of the invention, the coating 30 is co-extruded with the at least one filament.

In one preferred form of the invention, the taurolidine-containing coating 30 is co-extruded with the at least one filament, wherein the taurolidine is contained within a matrix which comprises matrix material plus taurolidine, and wherein the taurolidine-incorporating matrix material is the same matrix material as the remainder of the filament.

In one preferred form of the invention, the taurolidine-containing coating 30 is co-extruded with the at least one filament, wherein the taurolidine is contained within a matrix which comprises matrix material plus taurolidine, and wherein the taurolidine-incorporating matrix material is a different matrix material than the remainder of the filament.

Figure 8:
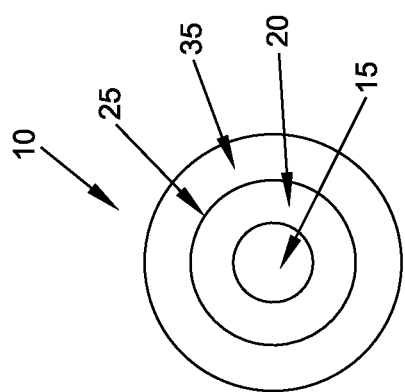
FIG. 8 is a schematic view of another novel filament formed in accordance with the present invention.

In one preferred form of the invention, and looking now at FIG. 8, the at least one filament further comprises an overcoating 35 disposed on top of the coating 30 of taurolidine.

In one preferred form of the invention, the antimicrobial suture comprises multiple filaments and the taurolidine is positioned in the interstitial spaces between the filaments.

In one preferred form of the invention, the antimicrobial suture comprises at least one filament and the at least one filament comprises a porous structure which has been exposed to taurolidine (e.g., dampened by, or immersed in, a solution containing taurolidine) such that taurolidine is present within the porous structure of the at least one filament.

In one preferred form of the invention, the antimicrobial suture comprises at least one filament which comprises a porous structure, and the antimicrobial suture is packaged immersed in, or dampened by, a solution comprising taurolidine (i.e., the antimicrobial suture is packaged "wet").

In one preferred form of the invention, the antimicrobial suture comprises at least one filament which comprises a porous structure, and the antimicrobial suture has been exposed to a solution containing taurolidine and then desiccated before packaging (i.e., the antimicrobial suture is packaged "dry").

In one preferred form of the invention, the proportion of taurolidine in the antimicrobial suture constitutes greater than about 1% by weight.

In one preferred form of the invention, the proportion of taurolidine in the antimicrobial suture constitutes greater than about 2% by weight.

In one preferred form of the invention, the proportion of taurolidine in the antimicrobial suture constitutes greater than about 6% by weight.

In one preferred form of the invention, the proportion of taurolidine in the antimicrobial suture constitutes greater than about 10% by weight.

Figure 9:
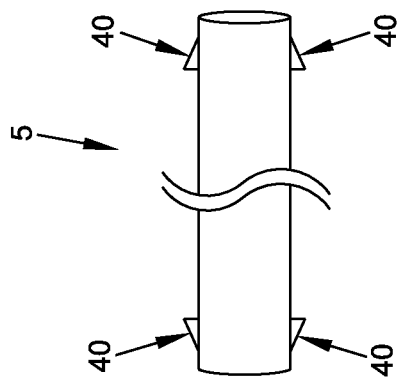
FIG. 9 is a schematic view of another novel filament formed in accordance with the present invention.

In one preferred form of the invention, and looking now at FIG. 9, the antimicrobial suture further comprises barbs 40.

In another preferred form of the invention, there is provided a method for treating a wound, the method comprising:

providing an antimicrobial suture comprising at least one filament and taurolidine carried by the at least one filament; and treating the wound with the antimicrobial suture.

Figure 10:
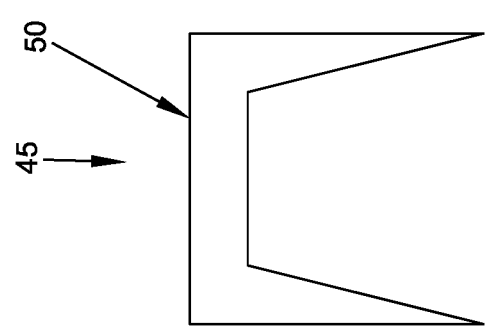
FIG. 10 is a schematic view of a novel antimicrobial staple formed in accordance with the present invention.

In another preferred form of the invention, and looking now at FIG. 10, there is provided an antimicrobial surgical staple 45. Antimicrobial surgical staple 45 generally comprises a surgical staple 50 and taurolidine carried by the surgical staple. By way of example but not limitation, antimicrobial surgical staple 45 may comprise a monofilament structure comprising taurolidine which has been incorporated into the monofilament structure, e.g., in a manner similar to how taurolidine is incorporated into the at least one filament of the antimicrobial suture discussed above.

In another preferred form of the invention, there is provided a method for treating a wound, the method comprising:

providing an antimicrobial surgical staple, the antimicrobial surgical staple comprising a surgical staple, and taurolidine carried by the surgical staple; and treating the wound with the antimicrobial surgical staple.

In accordance with the present invention, and by way of example but not limitation, a novel antimicrobial nylon suture may be provided, where the mono-filament type "thread" is similar to a plastic fishing line, except it is generally much thinner. The diameter of the nylon core of the suture is preferably about 2.5 decitex. "Decitex" is a measure of the thickness or diameter of a textile filament, and refers to the number of grams of weight of the yarn for each ten thousand meters of the yarn. As a more general proposition, the decitex number is a number used to define the size of the yarn, or the coarseness thereof, as generally a higher decitex number relates to a coarser yarn. To some extent, decitex also correlates to the strength of the yarn, as a higher decitex number tends to indicate a yarn that is stronger than one with a lower decitex number. In addition to its thickness, the strength of a particular yarn is also dependent upon the type of material used for the yarn. Nonetheless, for a particular type of yarn material, a higher decitex number will usually indicate a stronger yarn. Another analogous measurement parameter is the term "denier". Denier is an American unit of measure and relates to the weight of nine thousand meters of a yarn.

Various exemplary configurations of a novel antimicrobial suture are shown in FIGS. 11-13. The novel antimicrobial suture may comprise one or a plurality of individual structural filaments wherein the structural filaments have a structural portion that preferably comprises a nylon core. The nylon core may have an exterior surface that contains an antimicrobial portion. In another embodiment, the core of the nylon suture can optionally have no antimicrobial material while the sheath of the filament may contain the antimicrobial. Enough antimicrobial (e.g., taurolidine) is added to the matrix of the polymer or as a coating to the filament to provide antimicrobial properties to the suture while still maintaining the physical properties of the suture.

When determining the ratio between the amount of antimicrobial and the nylon or the filament(s), it is generally desirable to strike a balance. If too little antimicrobial is used, it is likely that the antimicrobial properties of the product will be adversely affected. If, on the other hand, too much antimicrobial is used, it may affect the material properties of the suture and/or result in the cost of the antimicrobial suture being driven up unnecessarily.

It is also generally desirable to strike a balance in the manufacturing of the antimicrobial suture. By way of example but not limitation, it is important to strike a balance on the extrusion temperature of the polymer (in the case of an extruded polymer filament) and the antimicrobial so that degradation of the antimicrobial is avoided in the manufacturing process.

In one form of the present invention, once extruded, the antimicrobial suture material is sent in a long length roll to the suture manufacturer. The suture manufacturer cuts the roll of suture "thread" into segments of predetermined sizes to create suture segments of desired lengths. A needle is typically then added to the cut suture segments. Typically, the finished suture/needle assembly is packaged so that the sutured thread and needle are sealed in a sterile plastic pouch.

The suture so formed will have a look and feel that is generally identical to the antimicrobial sutures currently on the market, such as the Triclosan sutures sold by Johnson & Johnson's ETHICON division. The suture is strong and pliable.

The suture described above is generally well adapted for use as an external suture. However, modifications may be preferable for sutures that are to be used internally. For example, rather than using an antimicrobial only near the surface of the filament, it may be preferable to use a suture containing the antimicrobial within the core of the suture.

Additionally, it is anticipated that there will be wide variations in packaging. For example, some packaged sutures may have a suture length of only several centimeters. Other sutures may extend for up to 40 meters, e.g., for tasks that require one very long suture. Examples of various types, sizes and lengths of sutures can be found at a plurality of web sites, such as www.suturedirect.com.

EXAMPLES

By way of example, the following evaluations were done to assess the performance of Taurolidine-containing antimicrobial sutures. Zone of Inhibition studies on 3 representative microorganisms, as well as solution exposure of the antimicrobial filaments immersed in early phase concentrations of 3 test microorganisms, were conducted.

Filament Preparation.

Filaments were prepared using taurolidine and 2 test polymers to represent suture materials. The polymers were poly ε-caprolactone and ρ-dioxanone. The taurolidine was extruded into the polymers by use of a Thermo Haake 16 mm Twin-Screw Extruder with a single hole die. The resulting structures were un-oriented filaments containing 2, 6 and 10% of taurolidine dispersed throughout the matrix of the filaments. Taurolidine was introduced as a powder while the polymers were provided as pellets. The filaments were then packaged prior to further evaluation.

Zone of Inhibition Evaluations.

Zone of Inhibition testing is a conventional method for estimating the inhibitory effects of antimicrobial substances against specific bacterial strains of interest. Zone of Inhibition assays are useful for testing diffusible agents. As the agent diffuses away from the disk, the concentration decreases logarithmically. The sensitivity of the organism to the agent is judged by the appearance and size of a zone where no growth occurs, i.e., the Zone of Inhibition.

Example 1

Demonstration of Zone of Inhibition of Taurolidine Impregnated in Poly ε-Caprolactone and ρ-Dioxanone 400 μl of early phase Pseudomonas aeruginosa (PA01), the Staphylococcus epidermidis (S. epi 35984), and the multidrug resistant Staphylococcus aureus (MRSA) strain SA BAA-44) were plated separately into square plates. 200 μl of each were introduced into 25 cm×25 cm plates and 100 μl were introduced into 15 cm×15 cm plates. Four pieces of each filament were individually placed in the plates. The filaments tested were taurolidine loaded at 2, 6 and 10% dispersed in poly ε-caprolactone and 2, 6, and 10% dispersed in ρ-dioxanone. After 24 hours of exposure the Zone of Inhibition surrounding each filament sample was measured in mm.

The results of the Zone of Inhibition studies are summarized in FIG. 14 (all measurements are in mm).

Clearly the Zone of Inhibition increases with the increase in concentration of taurolidine in each of the filaments tested.

Figure 15:
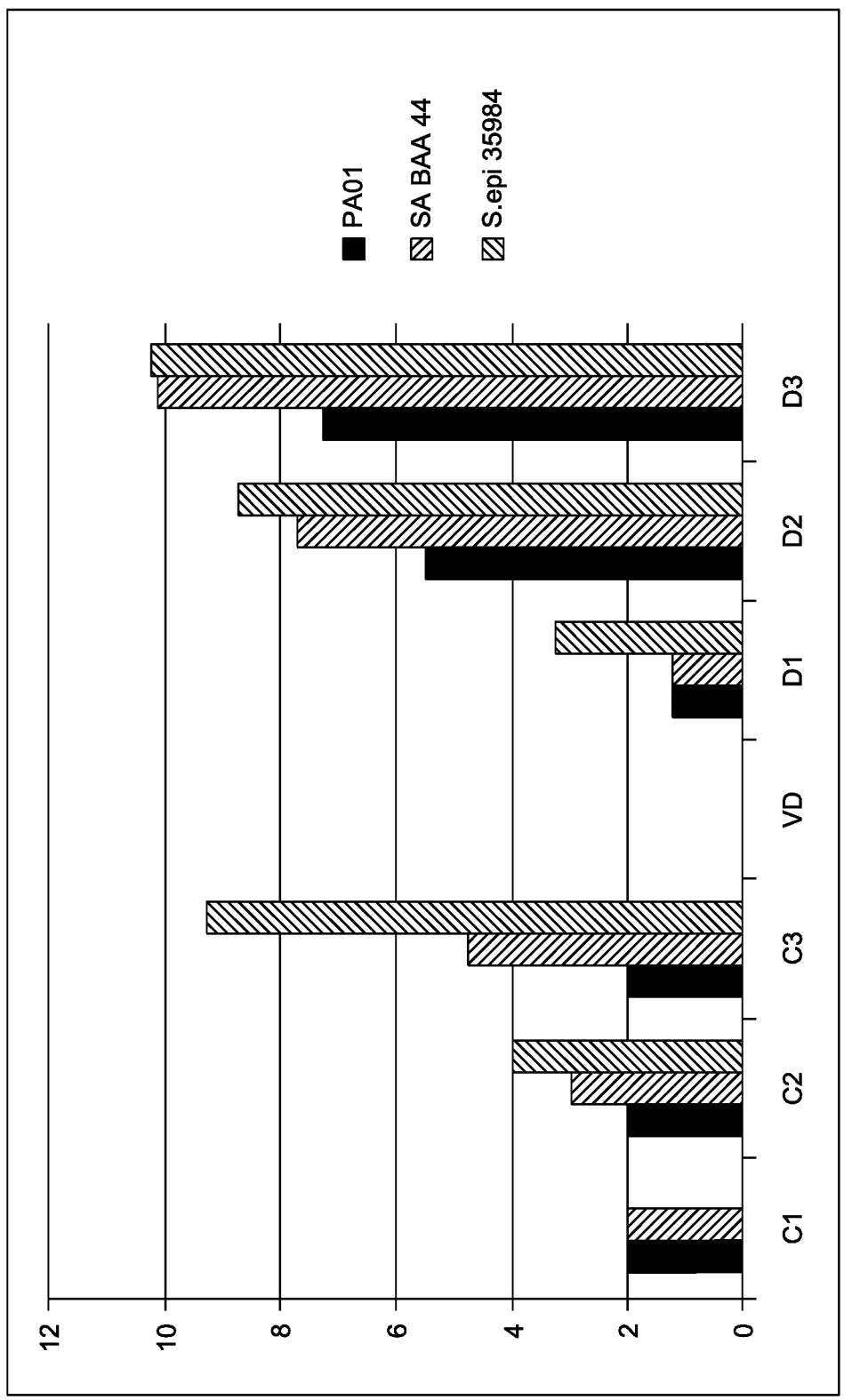
FIG. 15 is a graphic representation of the Zone of Inhibition data of FIG. 14, showing that the Zone of Inhibition increases with the increase in concentration of taurolidine in each of the filaments tested.

A graphic representation of the results is shown in the FIG. 15.

Figure 16:
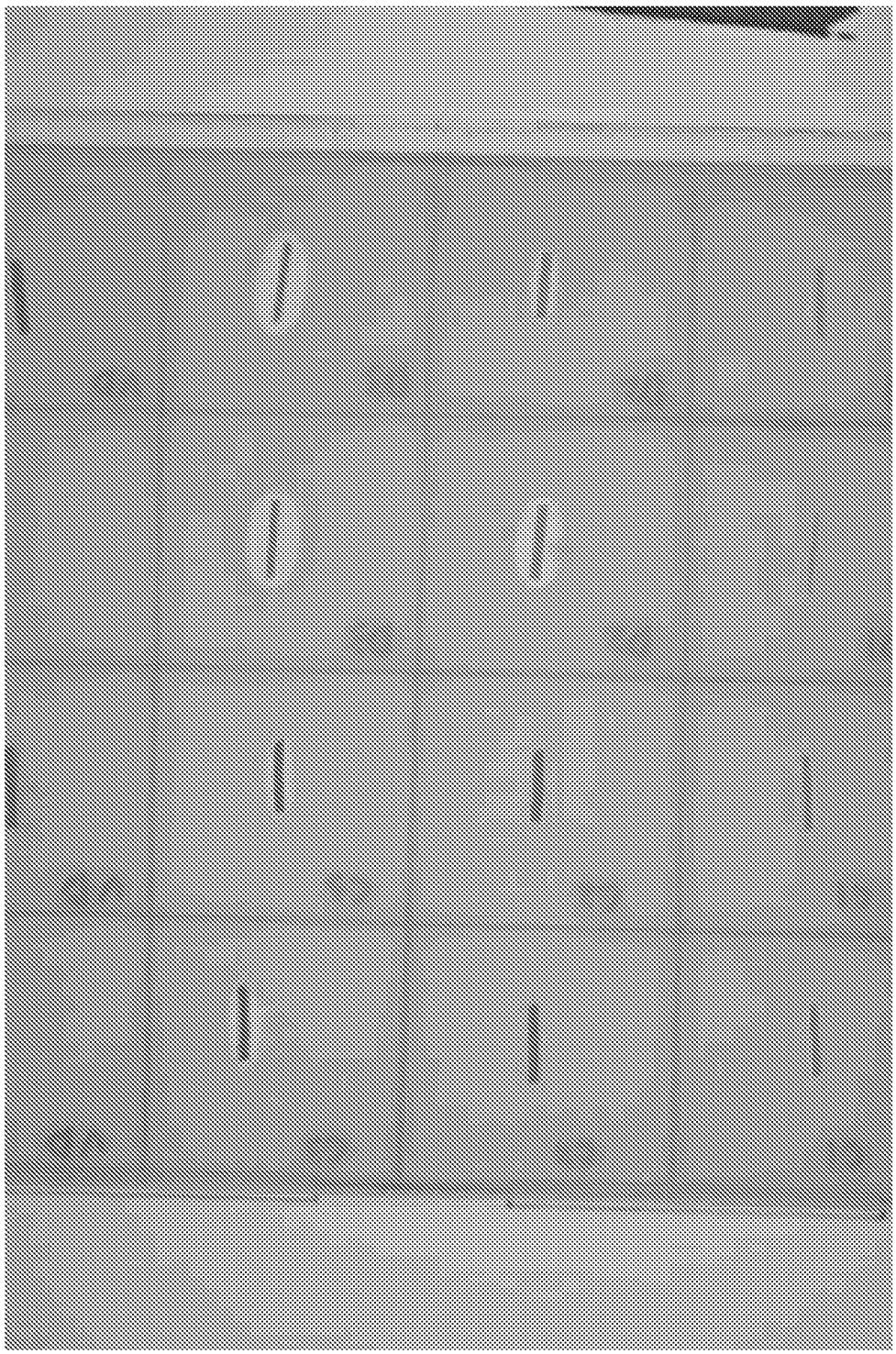
FIG. 16 shows representative Zones of Inhibition surrounding filaments that were tested.

FIG. 16 shows representative Zones of Inhibition surrounding the filaments that were tested.

Solution Exposure of Filaments to Living Cultures.

Further tests were conducted to determine the effects of the solution exposure of taurolidine-containing filaments to living cultures.

Example 2

Demonstration of Bacteria Kills with Drug-Loaded Filaments Placed in Solutions with Living Microorganisms (Solution Exposure Experiments)

In this study, each of the filaments was placed in 12 well-bottom culture discs that had 1 ml Tryptic Soy Buffer containing 100 μl of Early Phase Culture of each of the 3 bacteria: Pseudomonas aeruginosa (PA01), Staphylococcus epidermidis (S. epi 35984), and Multidrug Resistant Staphylococcus aureus (MRSA) strain SA BAA-44.) After 24 hours of exposure, the results shown in FIGS. 17, 18 and 19 were obtained for the three microorganisms tested.

Figure 17:
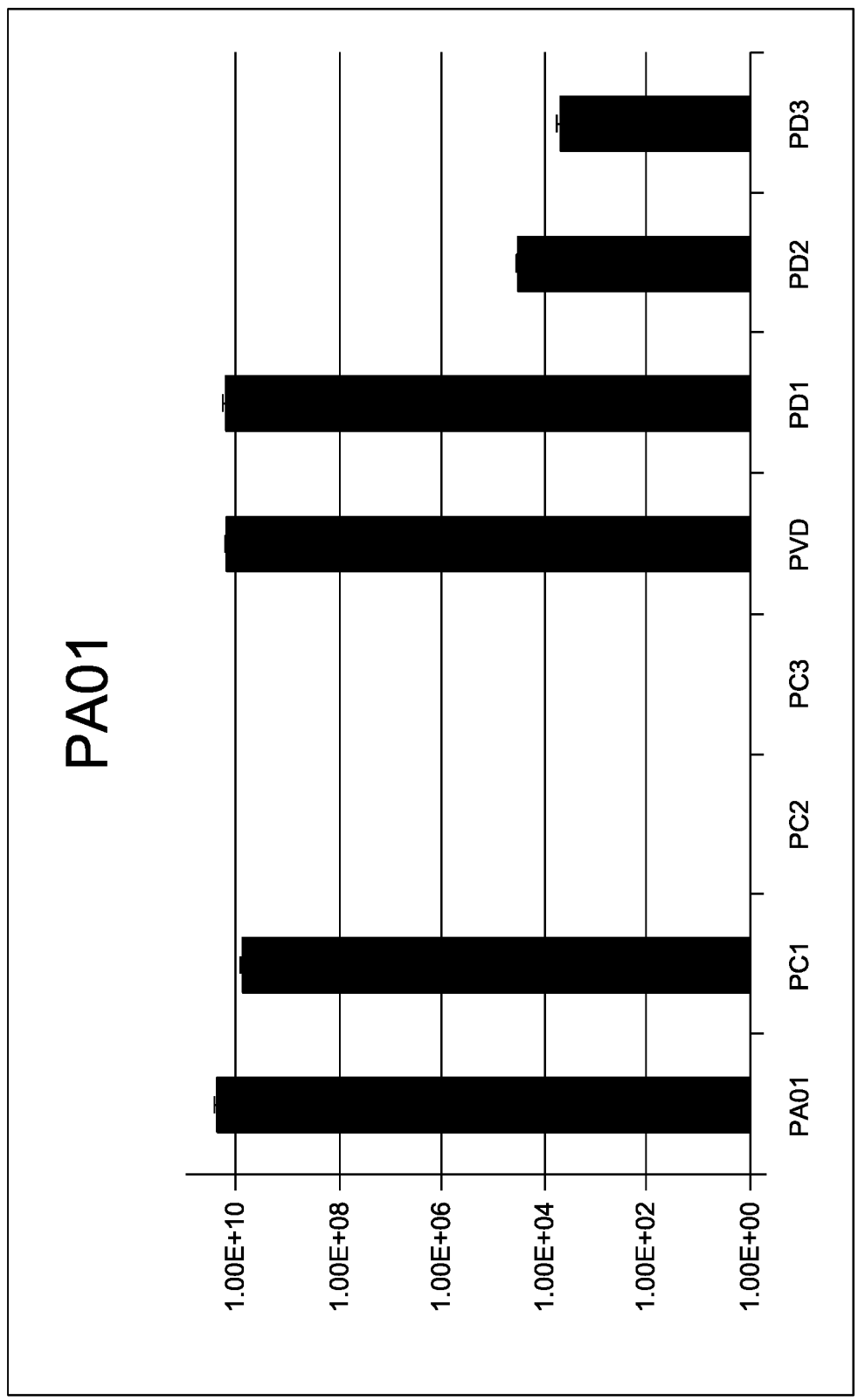
FIG. 17 is a graphic representation showing that for an initial concentration of Pseudomonas aeruginosa bacteria (PA01), the amount of kill observed by each test filament is correlated with the concentration of the taurolidine in each test filament.

More particularly, FIG. 17 shows that for an initial concentration of Pseudomonas aeruginosa bacteria (PA01), the amount of kill observed by each test filament correlated well with the concentration of the taurolidine in each. In FIG. 17, each filament tested was as follows:
 PC1=2% taurolidine in ε-caprolactone
 PC2=6% taurolidine in ε-caprolactone
 PC3=10% taurolidine in ε-caprolactone
 PVD=0% taurolidine in ρ-dioxanone
 PD1=2% taurolidine in ρ-dioxanone
 PD2=6% taurolidine in ρ-dioxanone
 PD3=10% taurolidine in ρ-dioxanone Total kills were observed for filaments that contained 6% or greater taurolidine in ε-caprolactone.

Figure 18:
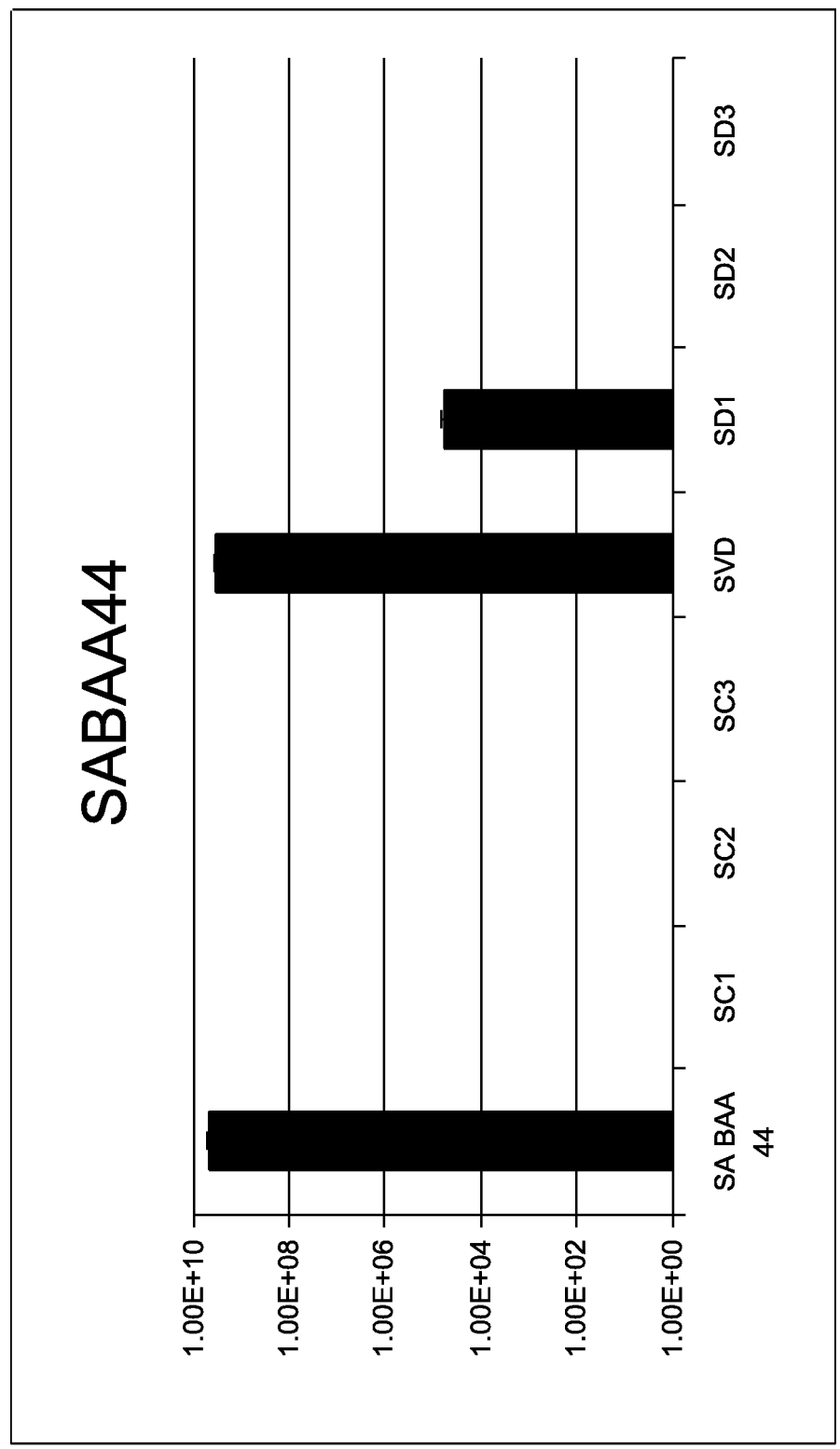
FIG. 18 is a graphic representation showing that for an initial concentration of Multidrug Resistant Staphylococcus aureus (MRSA) strain SABAA44, the amount of kill observed by each test filament is correlated with the concentration of the taurolidine in each test filament.

FIG. 18 shows that for an initial concentration of Multidrug Resistant Staphylococcus aureus (MRSA) bacteria strain SA BAA 44, the amount of kill observed by each test filament correlated well with the concentration of taurolidine in each. In FIG. 18, each filament tested was as follows:
 SC1=2% taurolidine in ε-caprolactone
 SC2=6% taurolidine in ε-caprolactone
 SC3=10% taurolidine in ε-caprolactone
 SVD=0% taurolidine in ρ-dioxanone
 SD1=2% taurolidine in ρ-dioxanone
 SD2=6% taurolidine in ρ-dioxanone
 SD3=10% taurolidine in ρ-dioxanone Total kills were observed for all the ε-caprolactone filaments that contained 2% or greater taurolidine and 6% or greater taurolidine in ρ-dioxanone.

Figure 19:
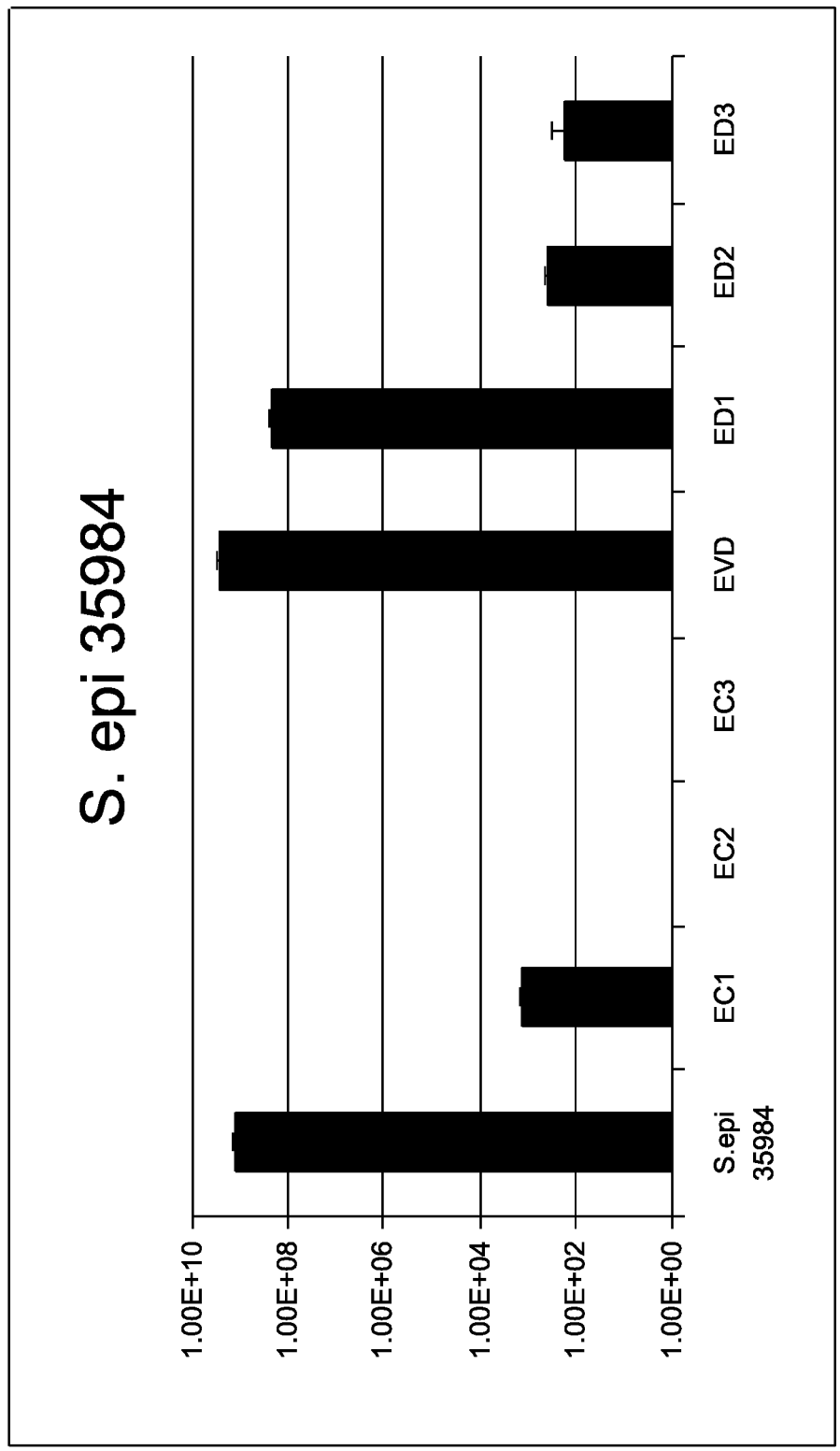
FIG. 19 is a graphic representation showing that for an initial concentration of Staphylococcus epidermidis bacteria strain S. epi 35984, the amount of kill observed by each test filament is correlated with the concentration of the taurolidine in each test filament.

FIG. 19 shows that for an initial concentration of Staphylococcus epidermidis bacteria strain S. epi 35984, the amount of kill observed by each test filament correlated well with the concentration of taurolidine in each. In FIG. 19, each filament tested was as follows:
 EC1=2% taurolidine in ε-caprolactone
 EC2=6% taurolidine in ε-caprolactone
 EC3=10% taurolidine in ε-caprolactone
 EVD=0% taurolidine in ρ-dioxanone
 ED1=2% taurolidine in ρ-dioxanone
 ED2=6% taurolidine in ρ-dioxanone
 ED3=10% taurolidine in ρ-dioxanone In FIG. 19 it is seen that filaments containing 6% or greater taurolidine in ε-caprolactone resulted in total kill of S. epidermidis.

Additional Examples

It is possible to create a filament wherein the composition of the filament, and the quantity of taurolidine carried by that filament, varies. See, for example, FIG. 20 which shows the composition of ten exemplary filaments.

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An antimicrobial suture comprising at least one filament and an antimicrobial consisting of taurolidine carried by said at least one filament;
 wherein said at least one filament comprises a material selected from the group consisting of polyglycolide (PGA), poly-p-dioxanone, poly ε-caprolactone, poly (glycolide-trimethylene carbonate) block copolymer and glycolide-dioxanone-trimethylene carbonate tri-block copolymer;
 wherein said taurolidine is incorporated in a taurolidine-containing matrix of material;
 wherein said at least one filament is extruded;
 and further wherein said taurolidine-containing matrix of material is co-extruded with said at least one filament.

2. An antimicrobial suture according to claim 1 wherein said at least one filament comprises a single filament.

3. An antimicrobial suture according to claim 1 wherein said at least one filament comprises a plurality of filaments.

4. An antimicrobial suture according to claim 3 wherein said plurality of filaments adhere to one another so as to constitute a singular structure.

5. An antimicrobial suture according to claim 4 wherein said plurality of filaments are co-extruded so as to form a composite structure.

6. An antimicrobial suture according to claim 4 wherein said plurality of filaments are braided together so as to constitute a singular structure.

7. An antimicrobial suture according to claim 1 wherein said at least one filament is resorbable.

8. An antimicrobial suture according to claim 1 wherein said at least one filament is non-resorbable.

9. An antimicrobial suture according to claim 1 wherein said at least one filament comprises a polymer.

10. An antimicrobial suture according to claim 9 wherein said at least one filament comprises a homopolymer.

11. An antimicrobial suture according to claim 1 wherein said at least one filament comprises a copolymer.

12. An antimicrobial suture according to claim 1 wherein said at least one filament comprises a matrix of material.

13. An antimicrobial suture according to claim 12 wherein said taurolidine-containing matrix of material is disposed within said matrix of material.

14. An antimicrobial suture according to claim 12 wherein said taurolidine-containing matrix of material is substantially evenly dispersed within said matrix of material.

15. An antimicrobial suture according to claim 12 wherein said taurolidine is restricted to one or more regions of said matrix of material.

16. An antimicrobial material according to claim 15 wherein said at least one filament is extruded, and further wherein said taurolidine is co-extruded with said at least one filament.

17. An antimicrobial suture according to claim 16 wherein said taurolidine comprises a taurolidine-containing matrix of material, and further wherein the material of said taurolidine-containing matrix of material is the same as the material of said matrix of material of said filament.

18. An antimicrobial suture according to claim 16 wherein said taurolidine comprises a taurolidine-containing matrix of material, and further wherein the material of said taurolidine-containing matrix of material is different than the material of said matrix of material of said filament.

19. An antimicrobial suture according to claim 12 wherein the material of said taurolidine-containing matrix of material is the same as the material of said matrix of material of said filament.

20. An antimicrobial suture according to claim 12 wherein the material of said taurolidine-containing matrix of material is different than the material of said matrix of material of said filament.

21. An antimicrobial suture according to claim 1 further comprising an overcoating disposed on top of said taurolidine-containing matrix of material.

22. An antimicrobial suture according to claim 1 wherein the antimicrobial suture comprises multiple filaments, and further wherein the taurolidine is positioned in the interstitial spaces between the filaments.

23. An antimicrobial suture according to claim 1 wherein said at least one filament is absorbent, and further wherein a taurolidine solution is introduced into said at least one filament.

24. An antimicrobial suture according to claim 1 wherein the proportion of taurolidine in the antimicrobial suture constitutes greater than about 1% by weight.

25. An antimicrobial suture according to claim 1 wherein the proportion of taurolidine in the antimicrobial suture constitutes greater than about 2% by weight.

26. An antimicrobial suture according to claim 1 wherein the proportion of taurolidine in the antimicrobial suture constitutes greater than about 6% by weight.

27. An antimicrobial suture according to claim 1 wherein the proportion of taurolidine in the antimicrobial suture constitutes greater than about 10% by weight.

28. An antimicrobial suture according to claim 1 further comprising barbs.

29. A method for treating a wound, the method comprising:
   providing an antimicrobial suture comprising at least one filament and taurolidine carried by said at least one filament; and
   treating the wound with the antimicrobial suture.

30. An antimicrobial surgical staple comprising:
   a surgical staple; and
   taurolidine carried by said surgical staple.

31. A method for treating a wound, the method comprising:
   providing an antimicrobial surgical staple, the antimicrobial surgical staple comprising a surgical staple, and taurolidine carried by the surgical staple; and
   treating the wound with the antimicrobial surgical staple.

\* \* \* \* \*